United States Patent
Okiyama

(10) Patent No.: US 9,541,227 B2
(45) Date of Patent: Jan. 10, 2017

(54) MALE CONNECTOR EQUIPPED WITH LOCK MECHANISM

(71) Applicant: JMS CO., LTD., Hiroshima-shi, Hiroshima (JP)

(72) Inventor: Tadashi Okiyama, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 52 days.

(21) Appl. No.: 14/391,356

(22) PCT Filed: Apr. 5, 2013

(86) PCT No.: PCT/JP2013/060494
§ 371 (c)(1),
(2) Date: Oct. 8, 2014

(87) PCT Pub. No.: WO2013/154050
PCT Pub. Date: Oct. 17, 2013

(65) Prior Publication Data
US 2015/0247597 A1   Sep. 3, 2015

(30) Foreign Application Priority Data

Apr. 13, 2012  (JP) ................. 2012-092293

(51) Int. Cl.
*F16L 37/00* (2006.01)
*F16L 37/086* (2006.01)
(Continued)

(52) U.S. Cl.
CPC ........... *F16L 37/086* (2013.01); *A61M 39/045* (2013.01); *A61M 39/1011* (2013.01); *F16L 21/08* (2013.01); *A61M 2039/1027* (2013.01)

(58) Field of Classification Search
USPC ...................... 285/308, 305, 319
See application file for complete search history.

(56) References Cited

U.S. PATENT DOCUMENTS 5,688,254 A   11/1997  Lopez et al.
5,964,785 A   10/1999  Desecki et al.
(Continued)

FOREIGN PATENT DOCUMENTS

EP    0 459 812    12/1991
EP    2 298 406    3/2011
(Continued)

OTHER PUBLICATIONS

Extended European Search Report issued in European Application No. 13775248.1, Jul. 23, 2015, 7 pages.

*Primary Examiner* — Aaron Dunwoody
(74) *Attorney, Agent, or Firm* — Hamre, Schumann, Mueller & Larson, P.C.

(57) ABSTRACT

A lock mechanism includes a hood (20) that is arranged so as to surround the periphery of a male member (10) and is for insertion of a female connector (100), and a single lock lever (30) having a cantilever support structure capable of elastic displacement. The lock lever (30) is arranged with the free end (30a) thereof on the tip side of the male member (10), with the fixed end (30b) thereof on the base end side of the male member (10), and with the lengthwise direction thereof being approximately parallel to the male member (10). The lock lever (30) includes a claw (34) for engaging with the female connector (100). An operation arm (35) protrudes from the face of the lock lever (30) on the side opposite to the male member (10), and extends toward the fixed end (30b) side. If a pressing force in the direction approaching the male member (10) is applied to the tip (35a) of the operation arm (35), the lock lever (30) undergoes elastic deformation such that the claw (34) moves away from the male member (10).

12 Claims, 13 Drawing Sheets

(51) Int. Cl.
*A61M 39/04* (2006.01)
*A61M 39/10* (2006.01)
*F16L 21/08* (2006.01)

(56) References Cited

U.S. PATENT DOCUMENTS

| | | |
|---|---|---|
| 6,213,996 B1 | 4/2001 | Jepson et al. |
| 6,468,251 B1 | 10/2002 | Yamanaka et al. |
| 7,770,938 B2 * | 8/2010 | Bauer ............... F16L 37/0985 |
| | | 285/305 |
| 2004/0243065 A1 | 12/2004 | McConnell et al. |
| 2005/0010238 A1 | 1/2005 | Potter et al. |
| 2010/0030194 A1 | 2/2010 | Yokota et al. |
| 2011/0175347 A1 | 7/2011 | Okiyama |
| 2011/0178493 A1 | 7/2011 | Okiyama |
| 2015/0105753 A1 | 4/2015 | Okiyama |

FOREIGN PATENT DOCUMENTS

| | | |
|---|---|---|
| JP | 2549223 B | 10/1996 |
| JP | 2002-528234 | 9/2002 |
| JP | 3389983 B | 3/2003 |
| JP | 2004-000483 | 1/2004 |
| WO | 97/36636 | 10/1997 |
| WO | 2010/061742 | 6/2010 |
| WO | 2010/061743 | 6/2010 |
| WO | 2011/145991 | 11/2011 |
| WO | 2012/170961 | 12/2012 |
| WO | 2013/154049 | 10/2013 |

* cited by examiner

A

B

MALE CONNECTOR EQUIPPED WITH LOCK MECHANISM

TECHNICAL FIELD

The present invention relates to a male connector that includes a lock mechanism for maintaining a state of connection to a female connector.

BACKGROUND ART

When giving a patient an infusion or blood transfusion or performing extracorporeal blood circulation in surgery, it is necessary to form a channel (transport line) for transporting a liquid such as a drug solution or blood. Transport lines generally are formed by connecting containers, various types of instruments, feed tubes, and the like. Also, when a drug solution to be administered to a patient is injected into a drug solution bag (container), it is necessary to connect the drug solution bag and a syringe or the like. In this way, a male connector and a female connector are used to interconnect different members detachably.

One known example of a female connector used in this application is a needleless port that has a disk-shaped partition wall member (hereinafter referred to as a "septum") that is made of an elastic material such as rubber and has a linear slit (incision) formed in the central portion (e.g., see Patent Document 1). By inserting a tubular male luer (male member), which does not have a sharp metal needle such as an injection needle attached thereto, into the slit in the septum, the needleless port and the male luer can be put in communication with each other. The slit in the septum immediately closes when the male luer is withdrawn from the needleless port.

There are cases where the drug solution contains a drug designated as a dangerous drug, such as some anticancer drugs. There are also cases where blood contains a pathogen or the like. Accordingly, it is necessary to avoid a situation where a connected male connector and female connector unintentionally become separated, and as a result a liquid such as a drug solution or blood leaks out and comes into contact with the operator's finger or the like, or the operator inhales vapor from the liquid.

In view of this, a male connector with a lock mechanism 900 has been proposed in which, as shown in FIGS. 12A and 12B, a male luer 910 is provided with a lock mechanism for maintaining a state in which the male luer 910 is connected to a needleless port (e.g., see Patent Documents 2 to 4). This lock mechanism includes a pair of lock levers 930 arranged so as to be approximately parallel to the male luer 910 and sandwich the male luer 910. The lock levers 930 are connected to a base end portion 919 of the male luer 910 via support pieces 931 provided at an approximately central position in the lengthwise direction of the lock levers 930. A claw 934 that engages with the needleless port is formed on one end of each of the lock levers 930, on the surface on the side that opposes the male luer. The end portions of the lock levers 930 on the side not provided with the claws 934 are operation portions 935 for operating the lock levers. When the operation portions 935 of the pair of lock levers 930 are pressed toward each other, the support pieces 931 undergo elastic deformation, and the lock levers 930 become displaced in the direction in which the claws 934 move away from the male luer 910. Numeral 920 indicates an approximately cylindrical hood that surrounds the male luer 910 and is fixed to the base end portion 919. The pair of lock levers 930 are arranged in notches provided in the hood 920.

Numeral 915 indicates a tubular portion that is in communication with the male luer 910 and is for connection to a flexible tube (not shown).

As shown in FIG. 13, the male luer 910 is inserted into a septum 951 of a needleless port 950, and the claws 934 provided on the tips of the pair of lock levers 930 are engaged with a step on the outer circumferential face of the needleless port 950. Accordingly, the state of connection of the needleless port 950 and the male luer 910 is locked. Even if the male connector 900 and the needleless port 950 are pulled away from each other, the male connector 900 and the needleless port 950 cannot be separated since the claws 934 of the lock levers 930 are engaged with the needleless port 950. The male connector 900 and the needleless port 950 can be separated by applying force F1 to the operation portions 935 of the pair of lock levers 930 in a direction in which they approach each other, so as to displace the lock levers 930 and cancel the engagement between the claws 934 of the lock levers 930 and the needleless port 950.

PRIOR ART DOCUMENTS

Patent Document

[Patent Document 1] JP 3389983B
[Patent Document 2] JP 2004-483A
[Patent Document 3] WO 2010/061742
[Patent Document 4] WO 2010/061743

DISCLOSURE OF INVENTION

Problem to be Solved by the Invention

In the above-described conventional lock mechanism having a pair of lock levers 930, the claws 934 of the respective lock levers 930 in the pair engage with the needleless port 950. Accordingly, the two claws 934 need to be freed from the needleless port 950 in order to cancel the locked state achieved by the lock levers 930. However, even if the pressing force F1 is applied to the two operation portions 935 so as to widen the gap between the two claws 934, there are cases where the engagements of the two claws 934 to the needleless port 950 cannot be canceled at the same time. In this case, it is necessary to first cancel the engagement of one of the two claws 934 and then cancel the engagement of the other one while the gap between the two claws 934 is widened. Accordingly, there has been the problem that the operation for canceling the locked state is cumbersome.

Also, in order to cancel the locked state, it is necessary for the pressing force F1 in the direction in which the operation portions 935 approach each other to be applied to the operation portions 935 of the pair of lock levers 930. Specifically, the two operation portions 935 need to be pinched by the thumb and index finger of one hand, for example. At this time, the male connector 900 is held by only the two fingers placed on the two operation portions 935, and thus there has been the problem that the male connector 900 is held in an unstable manner.

An object of the present invention is to provide a male connector with a lock mechanism having improved operability and with which it is easy to perform the lock cancellation operation while stably holding the male connector.

Means for Solving Problem

A male connector with a lock mechanism of the present invention includes a bar-shaped male member for insertion into a female connector, and a lock mechanism for maintaining a state in which the male member is inserted into the female connector. The lock mechanism includes a hood that is arranged so as to surround a periphery of the male member and is for insertion of the female connector, and a single lock lever having a cantilever support structure capable of elastic displacement. The lock lever is arranged with a free end thereof on a tip side of the male member, with a fixed end thereof on a base end side of the male member, and with a lengthwise direction thereof being approximately parallel to the male member. The lock lever includes a claw for engaging with the female connector. An operation arm protrudes from a face of the lock lever on a side opposite to the male member, and extends toward the fixed end side. When a pressing force in a direction approaching the male member is applied to a tip of the operation arm, the lock lever undergoes elastic deformation such that the claw moves away from the male member.

Effects of the Invention

According to the lock mechanism of the present invention, the claw provided on the lock lever can be engaged with the female connector inserted into the hood, thus making it possible to maintain the state in which the male member is connected to the female connector. Also, since the portion of the male connector for engaging with the female connector is only one claw provided on a single lock lever, the locked state can be canceled easily by merely displacing the lock lever. Furthermore, since there is only one lock lever, it is possible to cancel the locked state with one finger while holding the hood or the like. Accordingly, it is possible easily to perform the lock cancellation operation while stably holding the male connector.

DESCRIPTION OF THE INVENTION

Figure 1:
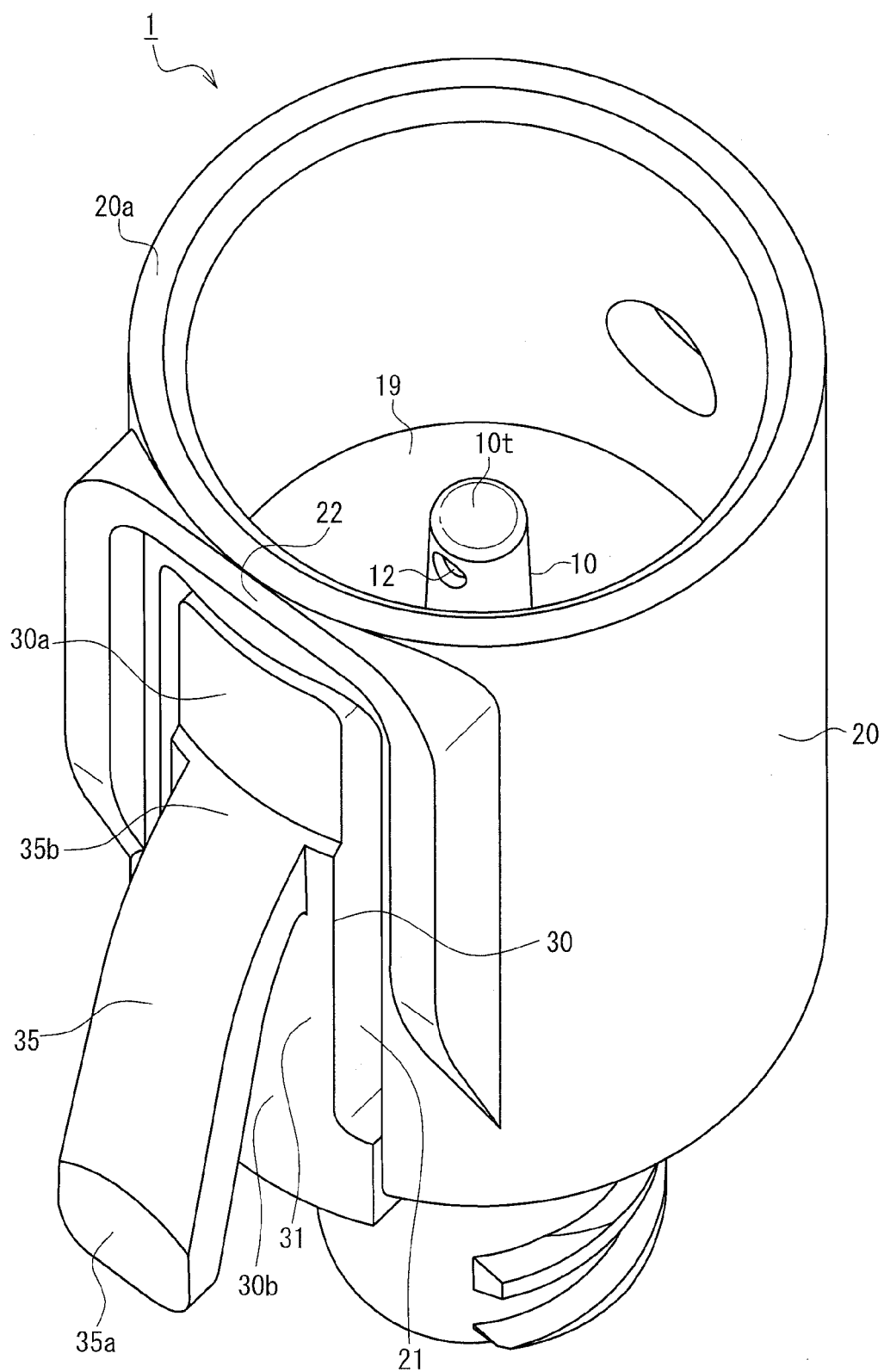
FIG. 1 is a perspective view of a male connector with a lock mechanism according to Embodiment 1 of the present invention.

A male connector with a lock mechanism of the present invention includes a bar-shaped male member for insertion into a female connector, and a lock mechanism for maintaining a state in which the male member is inserted into the female connector. The lock mechanism includes a hood that is arranged so as to surround a periphery of the male member and is for insertion of the female connector, and a single lock lever having a cantilever support structure capable of elastic displacement. The lock lever is arranged with a free end thereof on a tip side of the male member, with a fixed end thereof on a base end side of the male member, and with a lengthwise direction thereof being approximately parallel to the male member. The lock lever includes a claw for engaging with the female connector. An operation arm protrudes from a face of the lock lever on a side opposite to the male member, and extends toward the fixed end side. When a pressing force in a direction approaching the male member is applied to a tip of the operation arm, the lock lever undergoes elastic deformation such that the claw moves away from the male member.

In the above male connector with a lock mechanism of the present invention, it is preferable that the claw is provided on the free end of the lock lever. According to this, it is possible to increase the displacement amount of the claw when the lock lever is displaced. This makes it possible to cancel the locked state even if the pressing force applied to the tip (operation portion) of the operation arm is small, and this is advantageous in improving operability.

It is preferable that the operation arm is separated from the lock lever, with the exception of a base end of the operation arm. This is advantageous in displacing the lock lever such that the claw moves away from the male member when pressing force is applied to the tip (operation portion) of the operation arm.

It is preferable that the operation arm extends beyond the fixed end of the lock lever in the lengthwise direction of the male member. This is advantageous in displacing the lock lever such that the claw moves away from the male member when pressing force is applied to the tip (operation portion) of the operation arm.

It is preferable that a base end of the operation arm is provided at a position on the free end side relative to the fixed end of the lock lever. According to this, it is possible to ensure the elastic portion capable of elastic bending deformation between the base end of the operation arm and the fixed end of the lock lever. This is advantageous in elastically displacing the lock lever.

It is preferable that an approximately "U" shaped slit is formed in the hood. In this case, it is preferable that the lock lever is surrounded by the slit. According to this, the need to arrange the lock lever outside the hood is eliminated, thus making it possible to suppress the amount that the lock lever protrudes from the outer circumferential face of the hood. This enables a male connector having a small outer diameter to be achieved.

In the above, it is preferable that the hood includes a bridge portion on a side on which the female connector is inserted relative to the lock lever, and the bridge portion connects portions of the hood that sandwich the lock lever in a circumferential direction. According to this, even if an external force acts on the female connector in the state of being connected and locked to the male connector, it is possible to suppress inclination and movement of the female connector. As a result, it is possible to reduce the possibility of the locked state being unintentionally canceled and the hood becoming damaged.

It is preferable that a pair of notches that extend along a direction parallel to the male member are formed in an edge of the hood on a side on which the female connector is inserted. In this case, it is preferable that the pair of notches oppose each other across the male member. According to this, it is possible to realize a male connector that can be connected to a coinfusion port provided midway on a tube.

It is preferable that a channel is formed in the male member, and a lateral hole in communication with the channel is open at an outer circumferential face of the male member. When the male member that has been inserted into the female connector is withdrawn from the female connector, liquid attached to the periphery of the opening of the lateral hole is scraped away by the female connector, and therefore according to the above configuration, it is possible to reduce the amount of liquid that remains in the periphery of the opening of the lateral hole after withdrawal from the female connector.

The present invention will be described below in detail while disclosing preferred embodiments. However, it goes without saying that the present invention is not limited to the following embodiments. For the sake of convenience in the description, the drawings that are referenced in the following description show simplifications of, among the constituent members of the embodiment of the present invention, only relevant members that are necessary for describing the present invention. The present invention therefore can include arbitrary constituent members that are not shown in the following drawings. Also, regarding the dimensions of the members in the drawings, the dimensions of the actual constituent members, the ratios of the dimensions of the members, and the like are not shown faithfully.

Embodiment 1

Figure 2A:
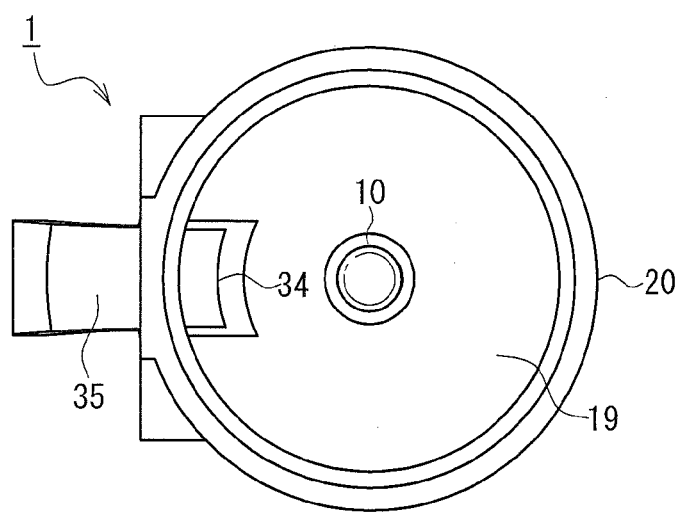
FIG. 2A is a plan view of the male connector with a lock mechanism according to Embodiment 1 of the present invention.
Figure 2B:
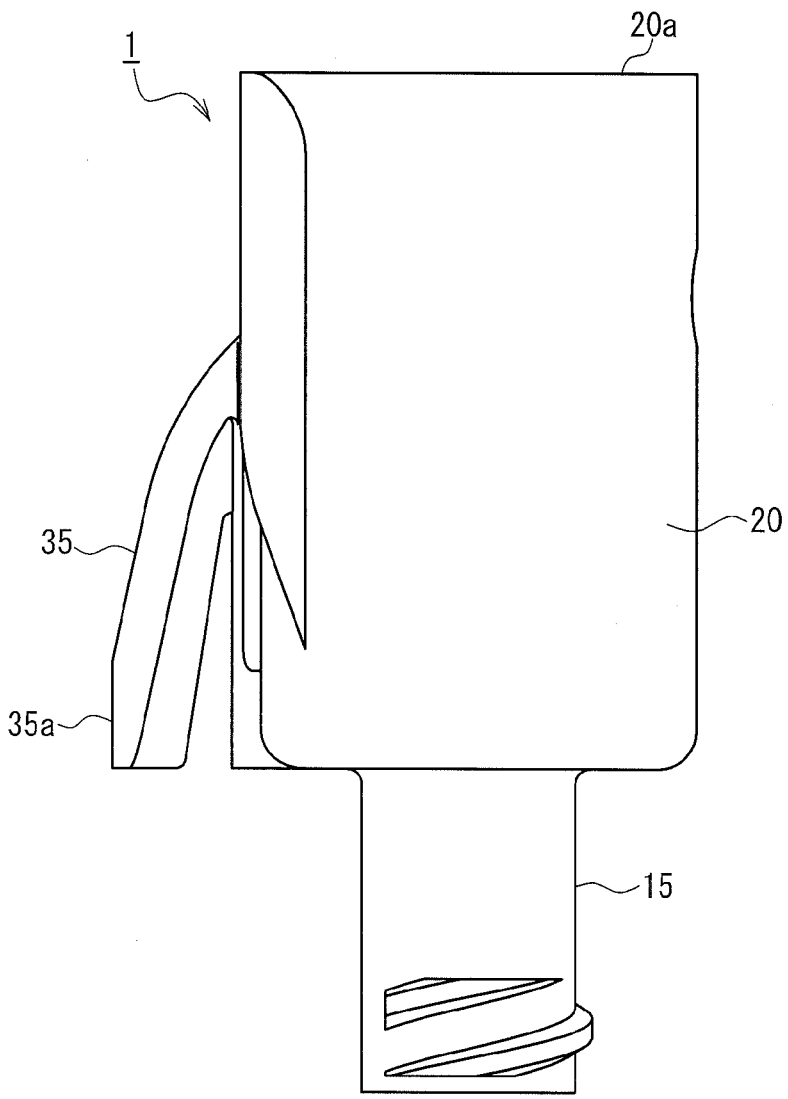
FIG. 2B is a side view of the same.

FIG. 1 is a perspective view of a male connector with a lock mechanism (referred to hereinafter as simply "male connector") 1 according to Embodiment 1 of the present invention. FIG. 2A is a plan view of the male connector 1, and FIG. 2B is a side view of the male connector 1. Furthermore, FIG. 3 is a cross-sectional perspective view of the male connector 1.

The male connector 1 of Embodiment 1 includes a bar-shaped male luer 10 as a male member. In FIG. 3, 10a indicates the central axis of the male luer 10. For convenience in the following description, the lengthwise direction of the male luer 10 (direction parallel to the central axis 10a) will be referred to as the "up-down direction", and the direction orthogonal to the lengthwise direction of the male luer 10 will be referred to as the "horizontal direction". Also, with regard to the up-down direction, the side close to a base 19 will be referred to as the "lower side", and the side far from it will be referred to as the "upper side" or the "tip side". Note that the "up-down direction" and the "horizontal direction" do not mean orientations during actual use of the male connector 1. Furthermore, the direction of a line orthogonal to the central axis 10a of the male luer 10 will be referred to as the "radial direction", and the direction of rotation about the central axis 10a will be referred to as the "circumferential direction".

Figure 3:
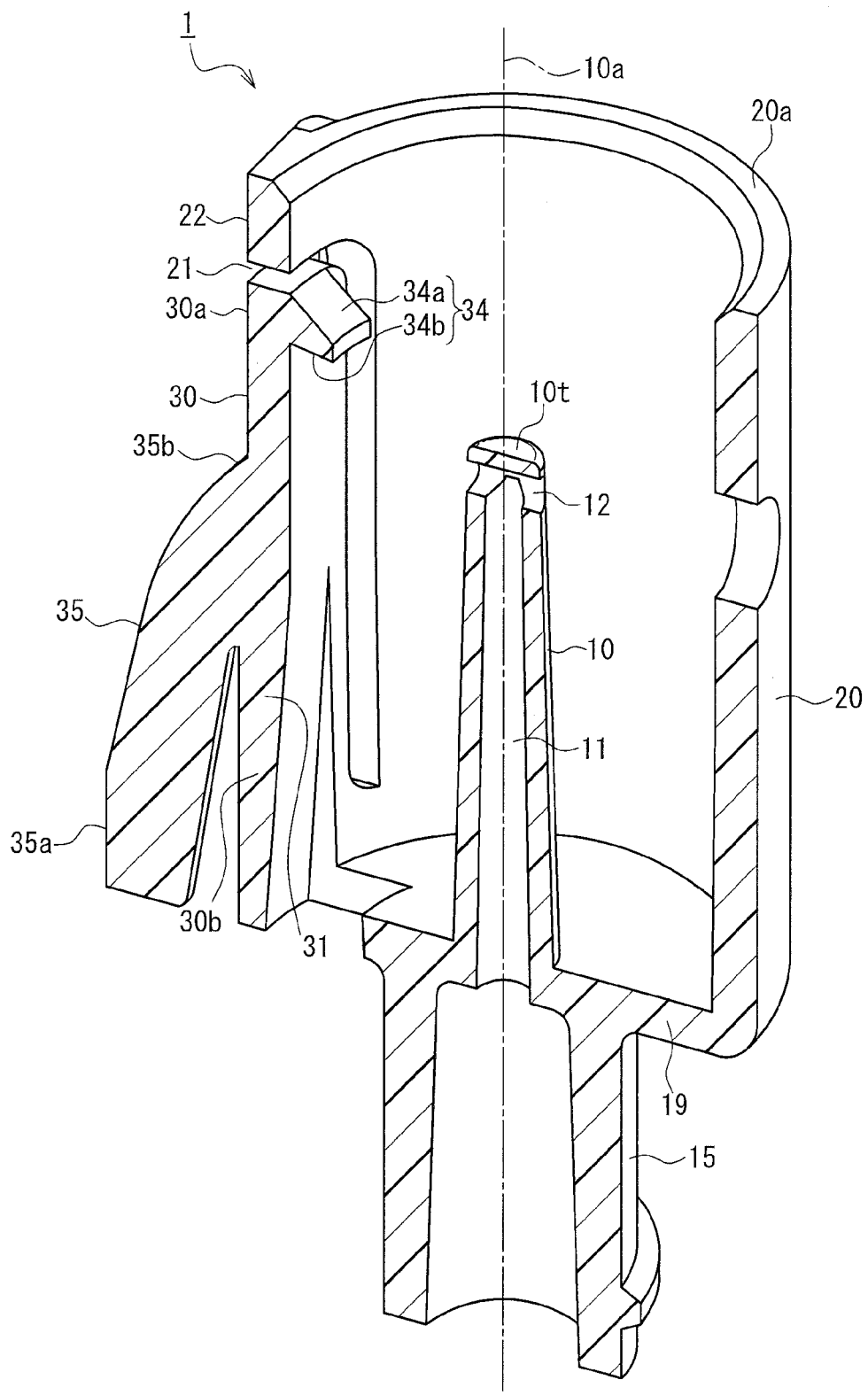
FIG. 3 is a cross-sectional perspective view of the male connector with a lock mechanism according to Embodiment 1 of the present invention.

As shown in FIG. 3, the male luer 10 is a bar-shaped member that protrudes from the base 19. The outer circumferential face (i.e., side face) of the male luer 10 is a tapered face such that the outer diameter slightly decreases with increasing distance from the base 19 in Embodiment 1. Note that the shape of the outer circumferential face of the male luer 10 is not limited to this, and any shape can be selected. For example, it may be a cylindrical face such that the outer diameter is constant in the up-down direction.

A channel 11 is formed in the male luer 10 along the lengthwise direction thereof. The channel 11 is not open at a tip face 10t of the male luer 10. Instead, a lateral hole 12 that is in communication with the channel 11 is formed in the vicinity of the tip of the male luer 10. The lateral hole 12 passes through the male luer 10 in the radial direction, and is open at two locations on the outer circumferential face of the male luer 10. Note that the lateral hole 12 may be open at only one location on the outer circumferential face of the male luer 10 instead of passing completely through male luer 10.

A tubular portion 15 that includes a channel in communication with the channel 11 is formed on the side of the base 19 opposite to the male luer 10. The inner circumferential face of the tubular portion 15 is a tapered face such that the inner diameter increases with increasing distance from the base 19. Female threading is formed on the outer circumferential face of the tubular portion 15. The tubular portion 15 can be configured in compliance with ISO594-2, for example. A syringe or the like can be connected to the tubular portion 15. Note that the configuration on the side opposite to the male luer 10 relative to the base 19 may be any configuration, and it may include a configuration other than the tubular portion 15.

A hood 20 is provided upright on the base 19 on the same side as the male luer 10 so as to surround the male luer 10. The hood 20 is shaped as a hollow cylinder that is coaxial with the male luer 10, and the height (up-down direction dimension) of the hood 20 is greater than the height of the male luer 10. The inner circumferential face of the hood 20 (the face opposing the male luer 10) is a cylindrical face having an inner diameter approximately the same as or slightly greater than the outer diameter of a female connector to which the male connector 1 of Embodiment 1 is to be connected.

A lock lever 30 having a cantilever support structure opposes the male luer 10. The lock lever 30 is shaped as a thin plate (shaped as a reed), and the lengthwise direction thereof is approximately parallel to the central axis 10a of the male luer 10. One end portion of the lock lever 30 in the lengthwise direction is a free end 30a, and this end portion is arranged on the tip side of the male luer 10. The other end portion of the lock lever 30 in the lengthwise direction is a fixed end 30b, and this end portion is arranged on the base end side (i.e., base 19 side) of the male luer 10. The lock lever 30 is capable of undergoing deformation so as to elastically bend in a plane that includes the central axis 10a of the male luer 10.

The lock lever 30 having a cantilever support structure is formed by providing the hood 20 with an approximately "U" shaped slit 21 that passes through the hood 20. In other words, the lock lever 30 is surrounded by the slit 21. As a result, a bridge portion 22 that connects portions of the hood 20 that sandwich the lock lever 30 in the circumferential direction is provided above (farther from the base 19 than) the free end 30a of the lock lever 30. An upper edge 20a of the hood 20 has a circular shape in a plan view, and is continuous in the circumferential direction with the same height.

As shown in FIG. 3, a claw 34 that protrudes toward the male luer 10 is formed on the face of the free end 30a of the lock lever 30 on the side that opposes the male luer 10. The claw 34 includes an inclined face 34a and an engaging face 34b. The inclined face 34a is inclined so as to move away from the male luer 10 with increasing distance from the base 19. The engaging face 34b is arranged on the base 19 side relative to the inclined face 34a, and is a flat face that is approximately parallel to the horizontal direction. As shown in FIG. 2A, the apex portion of the claw 34 (the portion closest to the male luer 10) protrudes to a position on the male luer 10 side relative to the inner circumferential face of the hood 20.

An operation arm 35 protrudes outward (away from the male luer 10) from the face of the lock lever 30 on the side opposite to the male luer 10. The portion of the operation arm 35 that is connected to the lock lever 30 will be referred to as a base end 35b. The operation arm 35 extends from the base end 35b in a curved manner toward the fixed end 30b side (i.e., downward) while moving away from the lock lever 30. In the up-down direction, the operation arm 35 extends to a position lower than the fixed end 30b of the lock lever 30 (to approximately the same position as the base 19 in Embodiment 1). An operation portion 35a is provided at the tip of the operation arm 35. The operation arm 35 has a mechanical strength according to which it can be considered to be substantially a rigid body.

Figure 4:
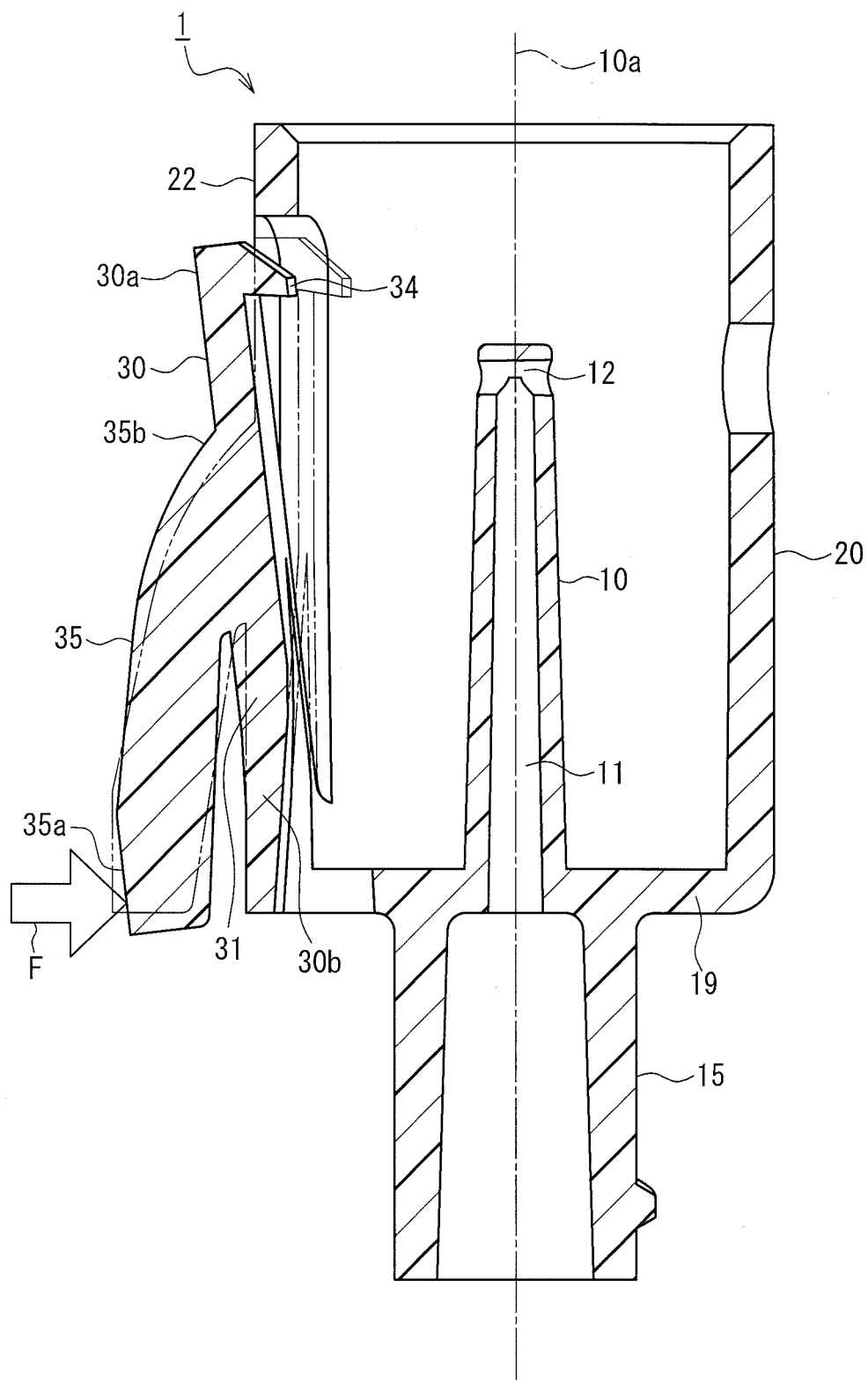
FIG. 4 is a side view of an elastically deformed lock lever in the male connector with a lock mechanism according to Embodiment 1 of the present invention.

If a finger presses against the operation portion 35a such that force F in the direction of approaching the male luer 10 (i.e., the hood 20) is applied to the operation portion 35a, the portion between the fixed end 30b of the lock lever 30 and the base end 35b of the operation arm 35 (i.e., an elastic portion 31) undergoes elastic bending deformation, and the claw 34 becomes displaced in a direction of separation from the male luer 10 approximately along the radial direction, as shown in FIG. 4.

In order to displace the claw 34 as described above, it is preferable that the operation arm 35 is separated from the fixed end 30b of the lock lever 30. Also, it is preferable that the operation arm 35 extends downward (toward the tubular portion 15 side) beyond the fixed end 30b of the lock lever 30, and that the operation portion 35a is located below (on the tubular portion 15 side relative to) the fixed end 30b. Furthermore, it is preferable that the base end 35b of the operation arm 35 is located on the free end 30a side relative to the fixed end 30b of the lock lever 30 (not including the case where the base end 35b is at the fixed end 30b).

The hood 20 and the lock lever 30 with the operation arm 35 described above configure the lock mechanism of the male connector 1 of Embodiment 1.

It is preferable that the male luer 10, the base 19, the hood 20, the lock lever 30, and the operation arm 35 are made of a hard material. Specifically, the male luer 10, the base 19, the hood 20, the lock lever 30, and the operation arm 35 can be created with a method such as integral molding, using a resin material such as polyacetal, polycarbonate, polystyrene, polyamide, polypropylene, or rigid polyvinyl chloride.

The following describes operations of and a method of use of the male connector 1 of Embodiment 1 configured as described above.

Figure 5:
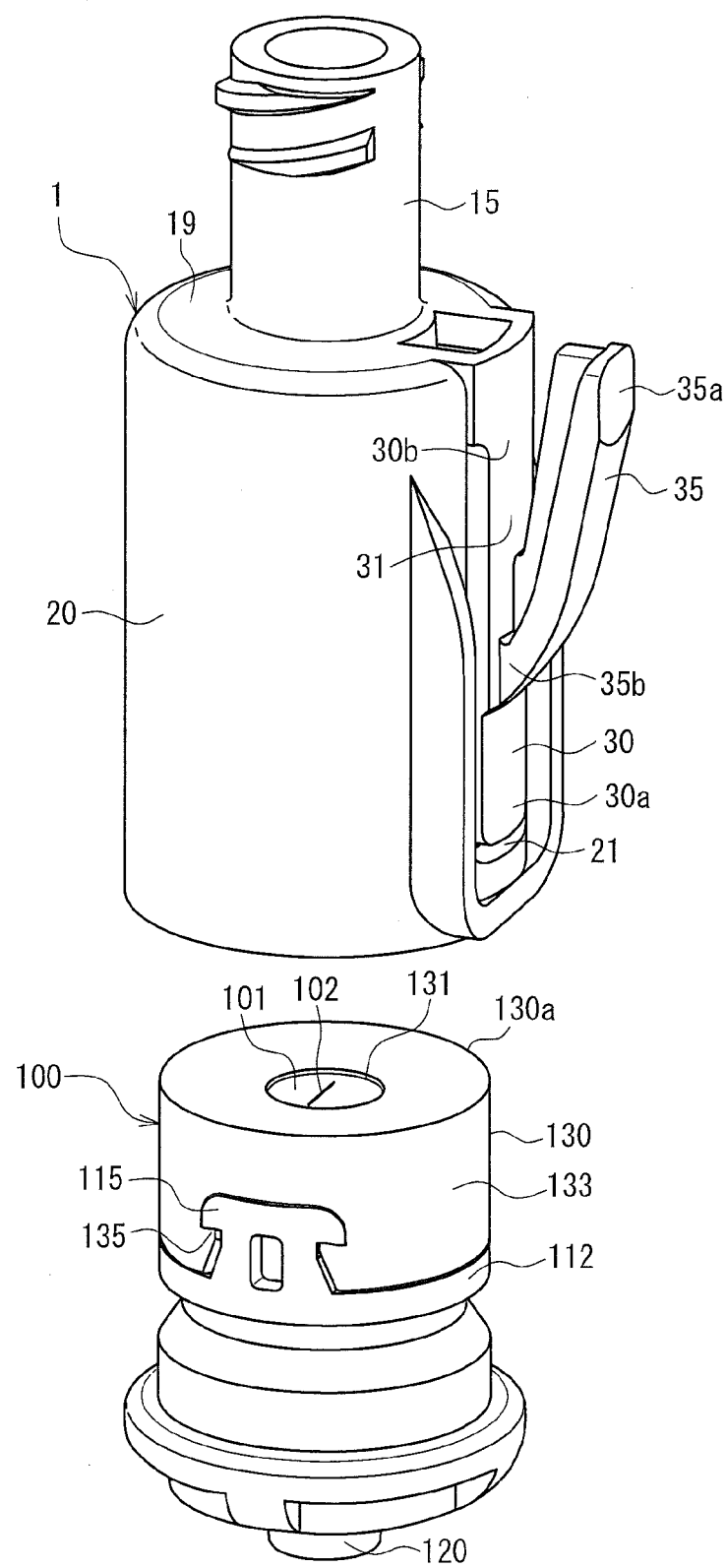
FIG. 5 is a perspective view of a female connector and the male connector with a lock mechanism according to Embodiment 1 of the present invention immediately before connection.
Figure 6:
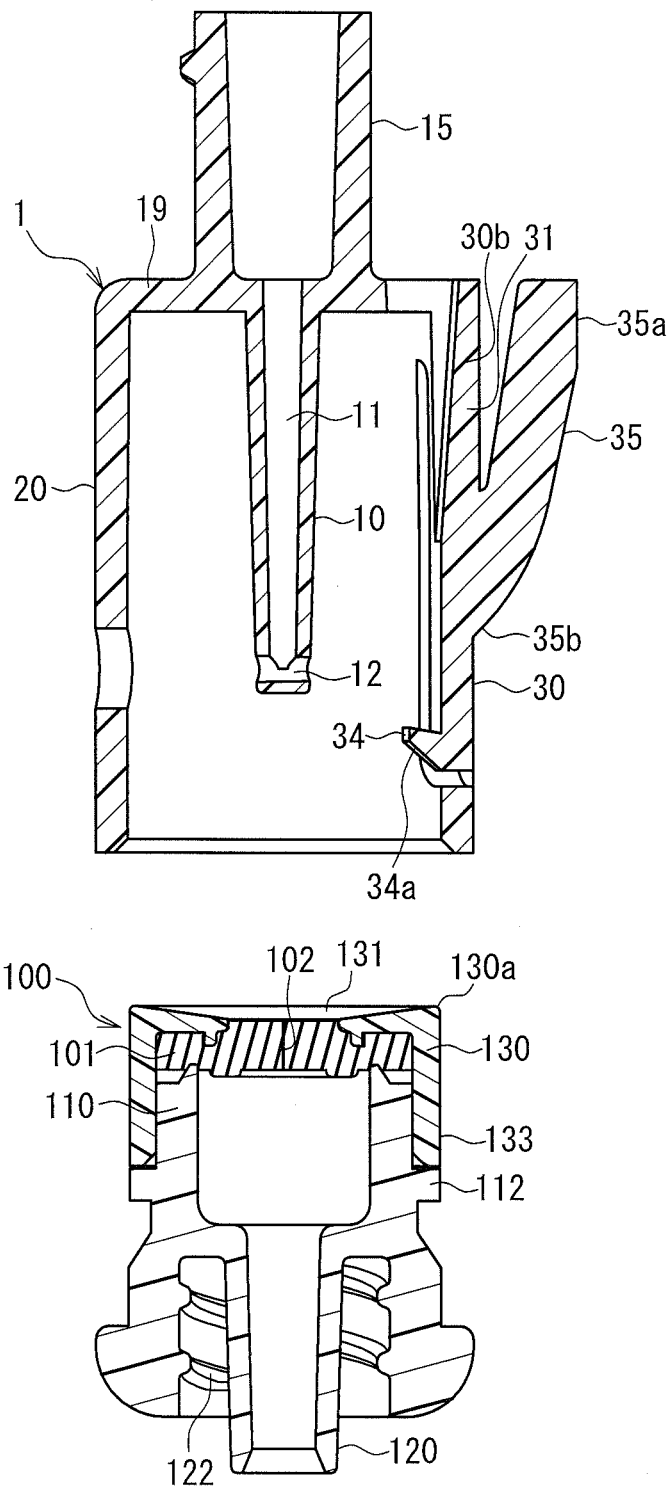
FIG. 6 is a cross-sectional view of the female connector and the male connector with a lock mechanism according to Embodiment 1 of the present invention immediately before connection.

FIG. 5 is a perspective view of the male connector 1 and a needleless port 100 serving as the female connector, immediately before connection. FIG. 6 is a cross-sectional view of the male connector 1 and the needleless port 100 immediately before connection.

The needleless port 100 includes disk-shaped partition wall member (septum) 101 that is made of an elastic material such as rubber and is provided with a linear slit (incision) 102 in the central portion. The septum 101 is placed at the tip of a tubular base portion 110, and is covered by cap 130. A locking claw 135 is formed by a notch in a cylindrical portion 133 encompassing the cap 130, and the cap 130 is fixed to the base portion 110 by engaging the locking claw 135 with a locking claw 115 formed on the outer circumferential face of the base portion 110. Accordingly, the septum 101 is sandwiched between the base portion 110 and the cap 130. An opening 131 is formed in the center of the cap 130, and the slit 102 in the septum 101 is exposed inside the opening 131. A protruding portion 112 is formed on the outer circumferential face of the base portion 110 on the side opposite to the septum 101, and protrudes so as to form a cylindrical face that is approximately the same as the cylindrical portion 133 of the cap 130. The protruding portion 112 is continuous in the circumferential direction of the base portion 110. A male luer 120 having a tapered outer circumferential face, and female threading 122 that is coaxial with the male luer 120, are provided on the side opposite to the base portion 110. Note that the configuration of the portions of the needleless port 100 on the side opposite to the base portion 110 are not limited to this, and these portions can have any configuration.

As shown in FIGS. 5 and 6, the male connector 1 is placed in opposition to the needleless port 100. The cap 130 of the needleless port 100 then is inserted into the hood 20 of the male connector 1, and then the needleless port 100 is pushed toward the male connector 1. The tip of the male luer 10 then comes into contact with the septum 101 that is exposed inside the opening 131 of the cap 130, and enters the slit 102. At the same time, the inclined face 34a of the claw 34 of the lock lever 30 comes into contact with an outer edge 130a of the cap 130. While sliding over the inclined face 34a, the edge 130a of the cap 130 causes the elastic portion 31 to undergo deformation so as to elastically bend, and displaces the lock lever 30 in the direction in which the claw 34 moves away from the male luer 10. As the needleless port 100 enters the hood 20, the claw 34 slides over the cylindrical portion 133 of the cap 130 and the protruding portion 112 in the stated order. Then, when the claw 34 has completely passed the protruding portion 112, the elastic portion 31 undergoes elastic restoration, and the claw 34 and the protruding portion 112 engage with each other (enter a locked state).

Figure 7:
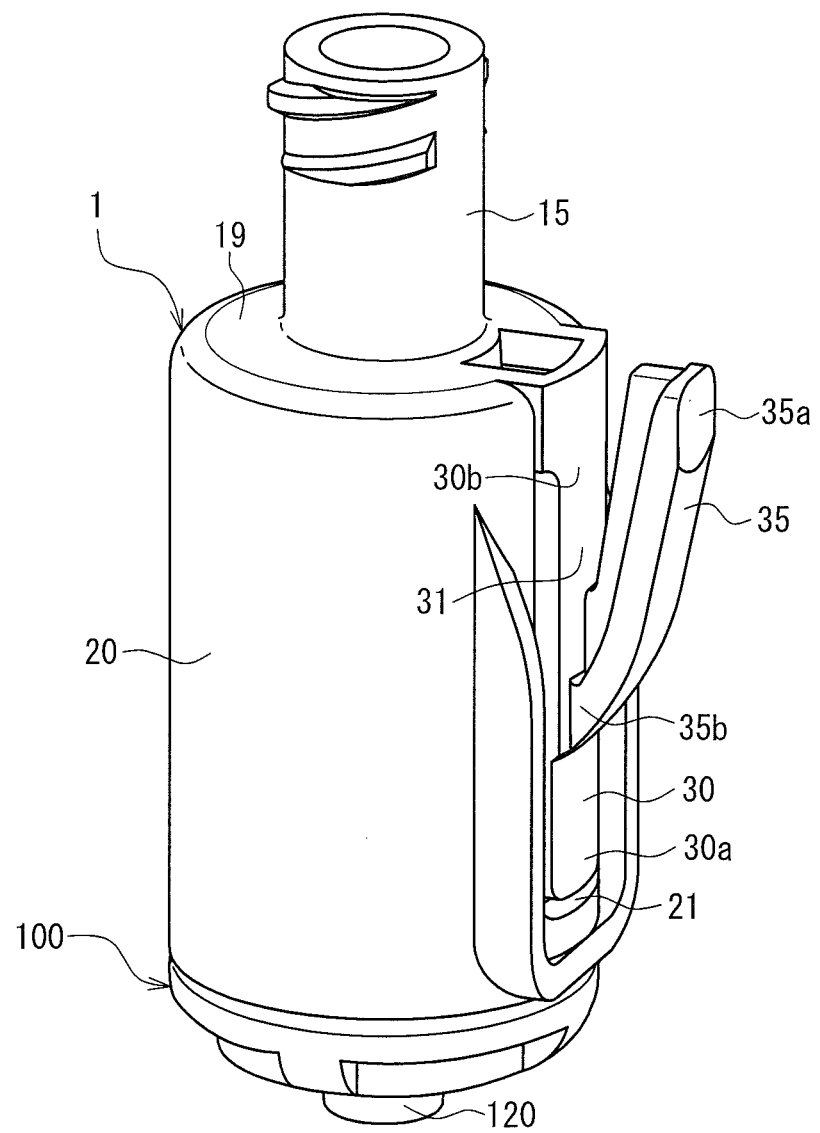
FIG. 7 is a perspective view of the female connector and the male connector with a lock mechanism according to Embodiment 1 of the present invention, in which the connected state is locked by the lock mechanism.
Figure 8:
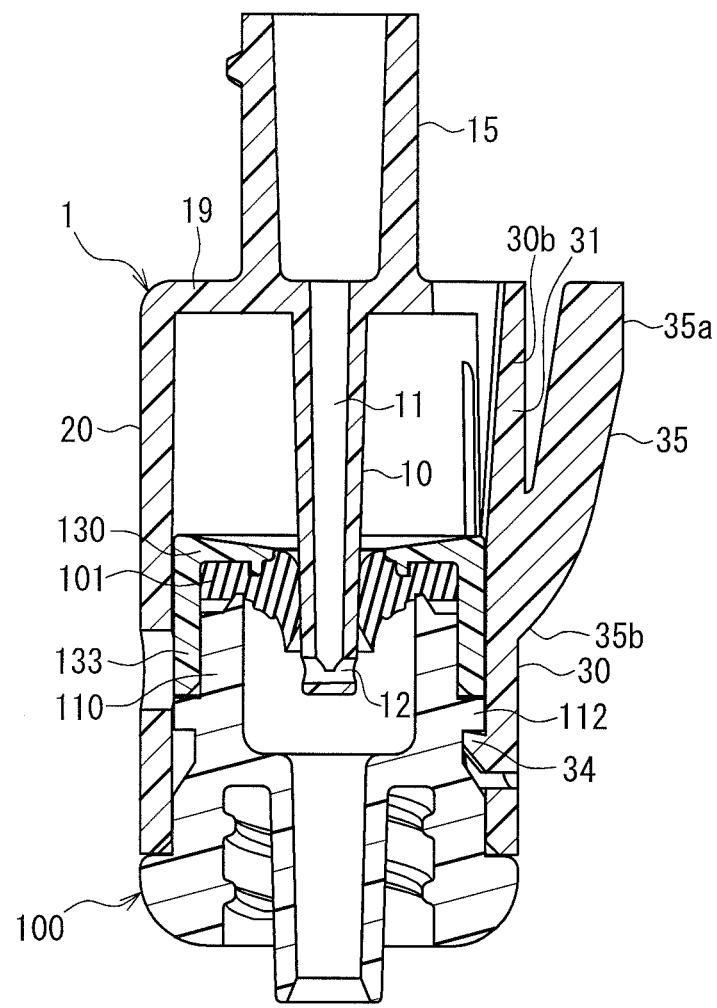
FIG. 8 is a cross-sectional view of the female connector and the male connector with a lock mechanism according to Embodiment 1 of the present invention, in which the connected state is locked by the lock mechanism.

FIG. 7 is a perspective view of the male connector 1 and the needleless port 100 in the connected and locked state. FIG. 8 is a cross-sectional view of the male connector 1 and the needleless port 100 in the connected and locked state.

The lock lever 30 is at approximately the same position as in the initial state (see FIGS. 1, 2A, 2B, and 3), and the claw 34 thereof (particularly the engaging face 34b thereof (see FIG. 3)) is engaged with the protruding portion 112 of the needleless port 100. The male luer 10 has passed through the slit 102 in the septum 101, and thus the septum 101 is undergoing a large amount of elastic deformation. The openings of the lateral hole 12 in the male luer 10 are exposed inside the inner cavity of the base portion 110. In this state, a liquid can be caused to flow between the male luer 10 and the needleless port 100 via the channel 11 and the lateral hole 12.

The male connector 1 and the needleless port 100 can be separated by pressing a finger against the operation portion 35*a* of the lock lever 30 and displacing the lock lever 30 in the direction in which the claw 34 moves away from the male luer 10 (see FIG. 4). The engagement between the claw 34 and the protruding portion 112 is thus canceled. If, at the same time, the needleless port 100 and the male connector 1 are pulled in the direction of separation from each other, the male connector 1 and the needleless port 100 can be separated. Immediately after the male luer 10 is withdrawn from the septum 101, the septum 101 undergoes elastic restoration, and the slit 102 closes.

As described above, according to Embodiment 1, in the state where the male luer 10 has passed through the septum 101, the claw 34 of the male connector 1 engages with the protruding portion 112 of the needleless port 100. Accordingly, the male luer 10 is prevented from unintentionally coming out of the septum 101.

With the male connector 1 of Embodiment 1, only one claw 34 is engaged with the protruding portion 112 of the needleless port 100. When the pressing force F is applied to the operation portion 35*a* so as to displace the claw 34, the needleless port 100 undergoes almost no movement due to being held by the hood 20. Accordingly, the engagement between the claw 34 and the protruding portion 112 can be canceled reliably by merely applying the pressing force F to the operation portion 35*a* so as to displace the claw 34.

Figure 13:
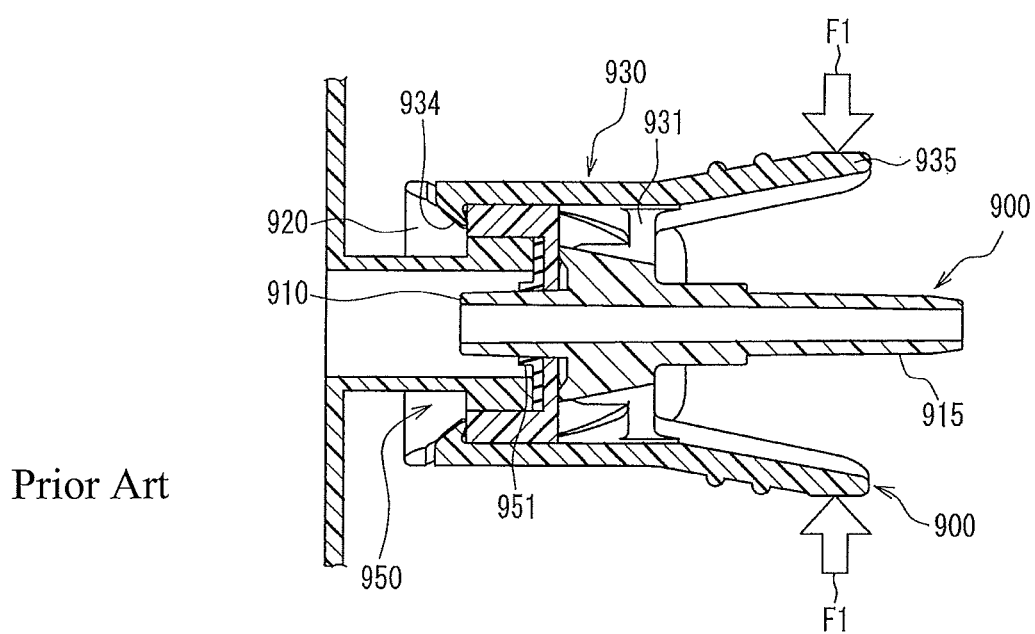
FIG. 13 is a cross-sectional view of the conventional male connector with a lock mechanism when connected to a needleless port.

As described above, with the conventional male connector 900 having a pair of lock levers 930 (see FIG. 13), two claws 934 engage with the needleless port 900, and thus there have been cases where canceling the locked state has required the engagement of the two claws 934 to be canceled one at a time in order. In contrast, with Embodiment 1, only one claw 34 for engagement with the needleless port 100 is provided, thus making it possible to cancel the locked state by merely applying the pressing force F (see FIG. 4) to the operation portion 35*a* so as to displace the lock lever 30. Accordingly, the operation for canceling the locked state is easy, and operability is improved.

Also, in Embodiment 1, it is only necessary to apply pressing force for causing the operation portion 35*a* to approach the hood 20 in order to cancel the engagement between the claw 34 and the protruding portion 112 (the locked state). This operation can be performed with only one finger of one hand. Accordingly, the hood 20 or the member connected to the tubular portion 15 can be held stably with the palm and remaining fingers of that one hand. For example, if the tip (i.e., opening) of the outer tube of a syringe is connected to the tubular portion 15, it is sufficient to press the operation portion 35*a* with the thumb or index finger of one hand while holding the outer tube of the syringe in that hand.

With the conventional male connector 900 having a pair of lock levers 930 (see FIG. 13), it has been necessary to pinch the two operation portions 935 with the thumb and index finger of one hand, for example, in order to cancel the locked state. At this time, the male connector 900 is held by only the two fingers placed on the two operation portions 935. Accordingly, there has been the problem that the operation for canceling the locked state is unstable. In contrast, with Embodiment 1, the locked state can be canceled with only one finger while holding the hood 20 or a member integrally connected to the male connector 1. Accordingly, the locked state can be canceled with only one finger while stably holding the male connector 1.

Arranging the claw 34 at a position farther from the fixed end 30*b* of the lock lever 30, preferably at the free end 30*a*, enables the displacement amount of the claw 34 to be increased. This makes it possible to cancel the locked state even if the pressing force F applied to the operation portion 35*a* is small, and this is advantageous in improving operability.

Since the inclined face 34*a* is formed on the claw 34 on the side opposite to the base 19, in the process of connecting the male connector 1 and the needleless port 100, the operator can engage the claw 34 and the protruding portion 112 by merely pressing the needleless port 100 into the hood 20, without needing to touch the lock lever 30 with his/her hand. The ease of performing the connection operation therefore is favorable.

Since the hood 20 surrounds the male luer 10, there is a reduced possibility of the operator mistakenly touching the male luer 10 with his/her hand. This is advantageous in keeping the operator away from dangerous drug solutions and blood.

Furthermore, the hood 20 contributes to the positioning of the needleless port 100 in the horizontal plane as well. Specifically, the hood 20 positions the needleless port 100 relative to the male luer 10 such that the male luer 10 is inserted precisely into the slit 102 in the septum 101 that is exposed inside the opening 131 of the cap 130. Also, the hood 20 positions the needleless port 100 relative to the lock lever 30 such that the claw 34 reliably engages with the protruding portion 112, or such that the engagement between the claw 34 and the protruding portion 112 is canceled reliably.

The approximately "U" shaped slit 21 is formed in the hood 20, and the lock lever 30 is surrounded by the slit 21. Accordingly, the lock lever 30 can be formed so as to approximately conform to the cylindrical face of the hood 20, thus making it possible to suppress the amount that the lock lever 30 protrudes from the outer circumferential face of the hood 20, in comparison to the case where the lock lever is arranged outward of (on the side opposite to the male luer 10 relative to) the outer circumferential face of the hood 20. This enables a small male connector 1 having a small outer diameter to be achieved.

The slit 21 formed in the hood 20 does not extend to the upper end of the hood 20. The hood 20 includes the bridge portion 22 at a position higher than the slit 21. As a result, the upper edge 20*a* of the hood 20 is continuous in the circumferential direction with the same height. This improves the strength of the upper edge 20*a* of the hood 20. Accordingly, in the case where external force in the horizontal direction acts on the needleless port 100 in the locked state (FIGS. 7 and 8), the hood 20 suppresses inclination and movement of the needleless port 100. This prevents the engagement between the claw 34 and the protruding portion 112 from being canceled by inclination or movement of the needleless port 100, thus reducing the possibility of the locked state being unintentionally canceled, and improving safety. Also, it is possible to prevent the hood 20 from being damaged by inclination or movement of the needleless port 100.

The channel 11 of the male luer 10 is not open at the tip face 10*t* of the male luer 10, and the lateral hole 12 in communication with the channel 11 is open at the outer circumferential face of the male luer 10. When the male luer 10 that has passed through the septum 101 is withdrawn from the septum 101 at a later time, liquid attached to the periphery of the openings of the lateral hole 12 is likely to be scraped away by the edges of the slit 102 in the septum 101, and therefore the above configuration is advantageous in reducing the amount of liquid that remains in the periphery of the openings of the lateral hole 12 after withdrawal from the septum 101.

Embodiment 2

Figure 9:
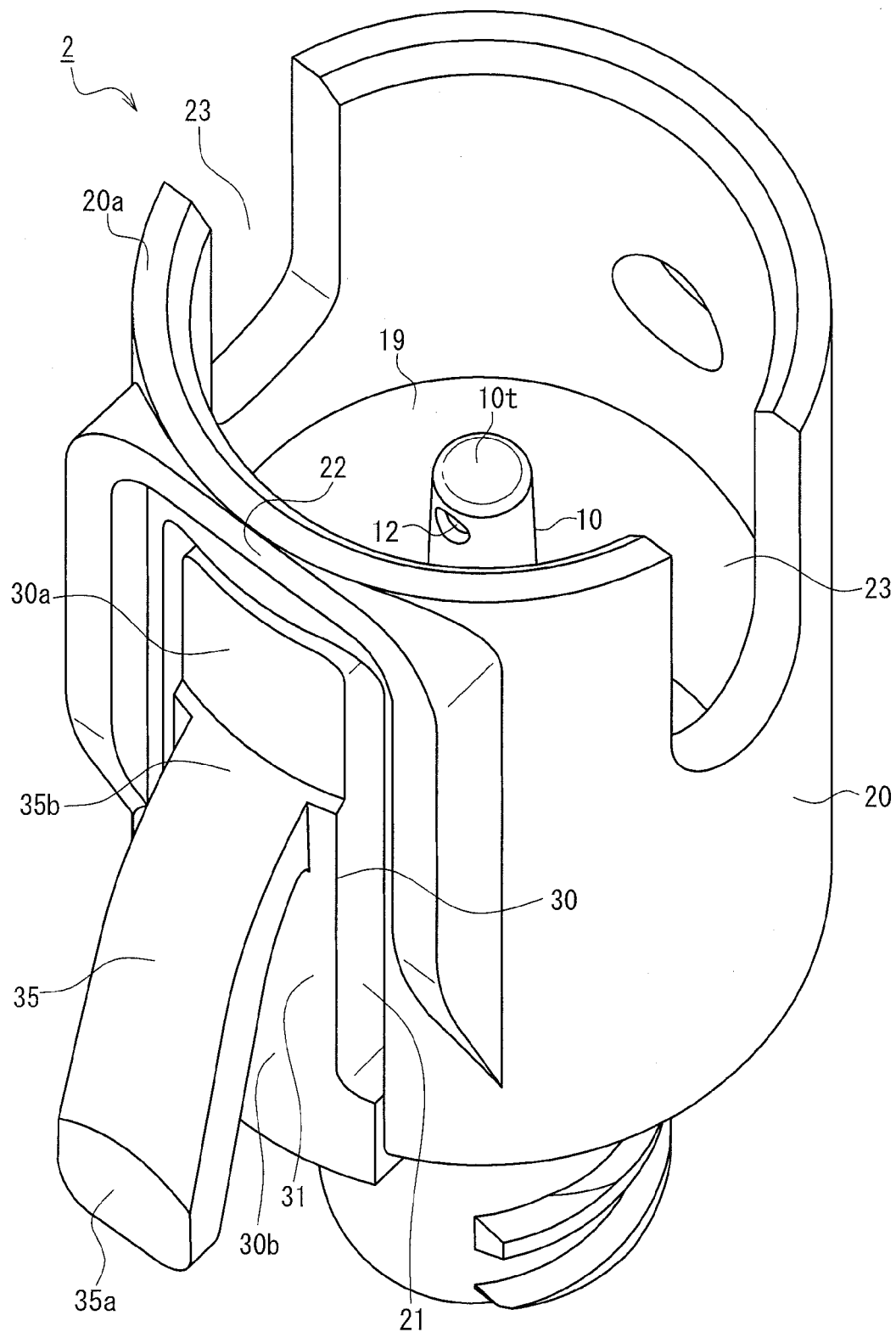
FIG. 9 is a perspective view of a male connector with a lock mechanism according to Embodiment 2 of the present invention.

FIG. 9 is a perspective view of a male connector with a lock mechanism (referred to hereinafter as simply "male connector") 2 according to Embodiment 2 of the present invention. The male connector 2 of Embodiment 2 differs from the male connector 1 of Embodiment 1 in that a pair of notches 23 that extend from the upper edge 20a of the hood 20 toward the base 19 parallel to the male luer 10 are formed in the hood 20. The pair of notches 23 oppose each other across the male luer 10, and the direction in which the pair of notches 23 oppose each other is approximately orthogonal to the direction in which the lock lever 30 and the male luer 10 oppose each other.

The following describes operations of and a method of use of the male connector 2 of Embodiment 2 configured as described above.

Figure 10:
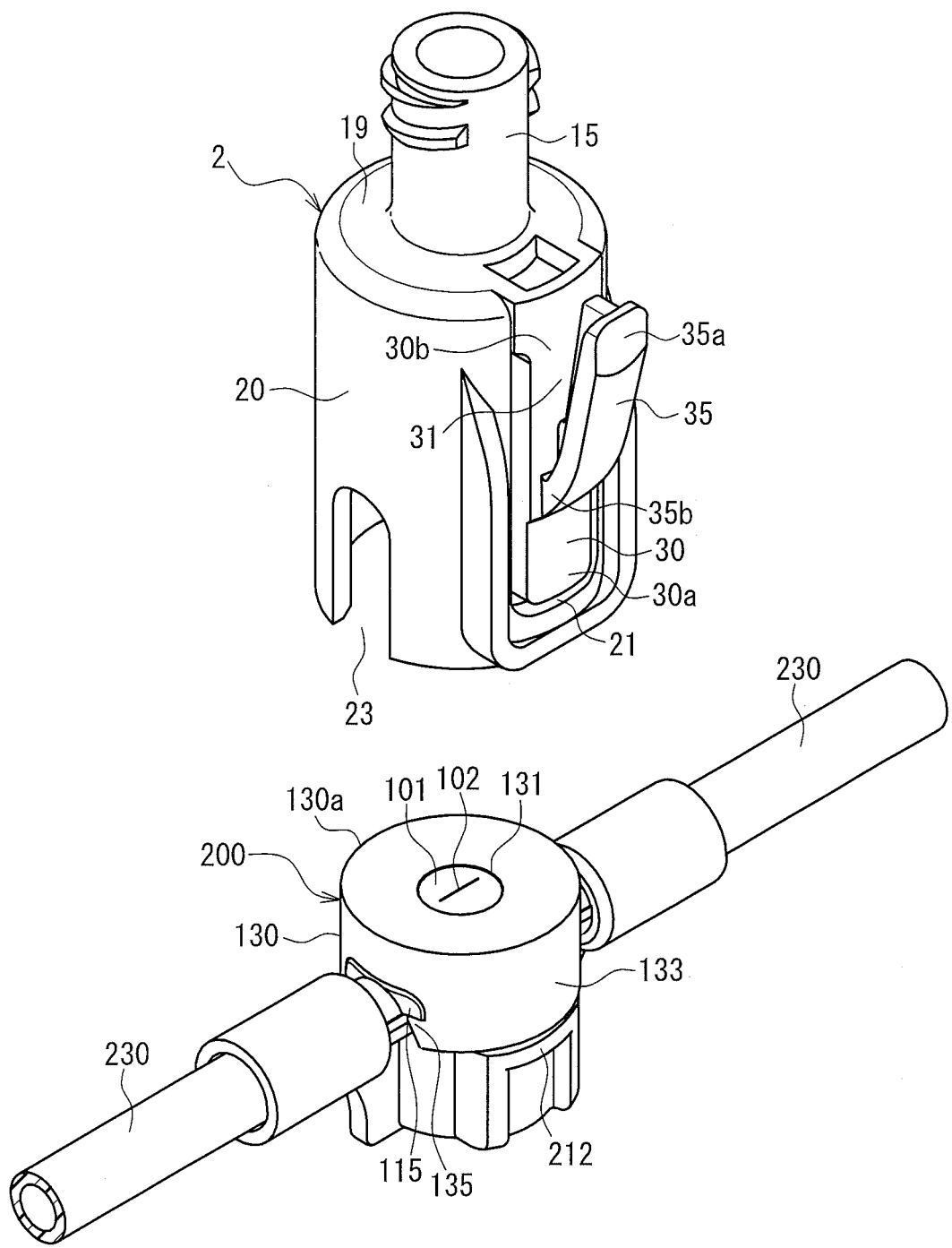
FIG. 10 is a perspective view of a female connector and the male connector with a lock mechanism according to Embodiment 2 of the present invention immediately before connection.

FIG. 10 is a perspective view of the male connector 2 and a needleless port 200 serving as the female connector, immediately before connection. In Embodiment 2, the needleless port 200 is provided midway on a flexible tube 230, and functions as a so-called coinfusion port (e.g., see Patent Document 1). The configuration of the needleless port 200 is roughly the same as that of the needleless port 100 of Embodiment 1. Although the protruding portion 112 that is continuous in the circumferential direction is formed in the needleless port 100 of Embodiment 1, a protruding portion 212 is formed in only a portion in the circumferential direction in the needleless port 200 of Embodiment 2. The claw 34 formed on the lock lever 30 engages with this protruding portion 212.

As shown in FIG. 10, the male connector 2 is placed in opposition to the needleless port 200. The cap 130 of the needleless port 200 is then inserted into the hood 20 of the male connector 2, and then the needleless port 200 is pushed toward the male connector 2.

Figure 11:
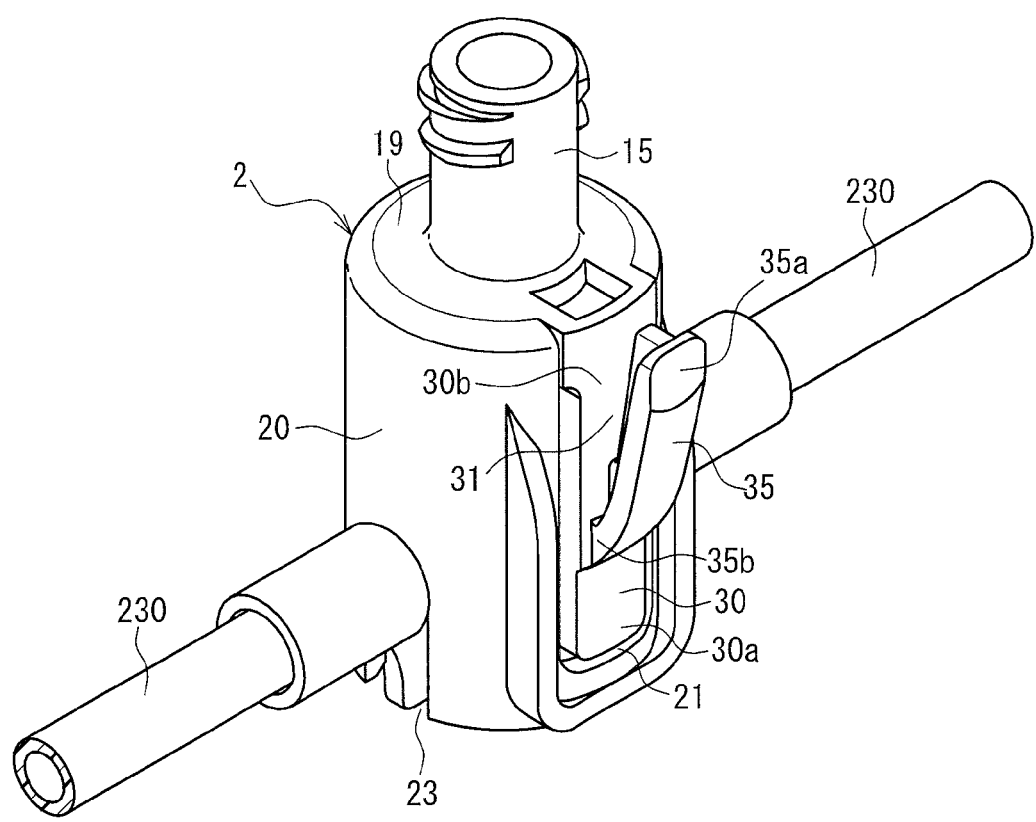
FIG. 11 is a perspective view of the female connector and the male connector with a lock mechanism according to Embodiment 2 of the present invention, in which the connected state is locked by the lock mechanism.
Figure 12A:
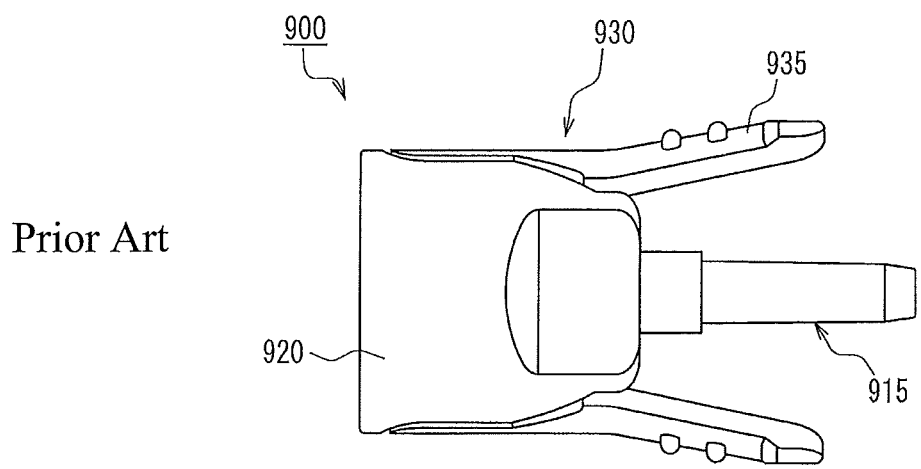
FIG. 12A is a side view of a conventional male connector with a lock mechanism.
Figure 12B:
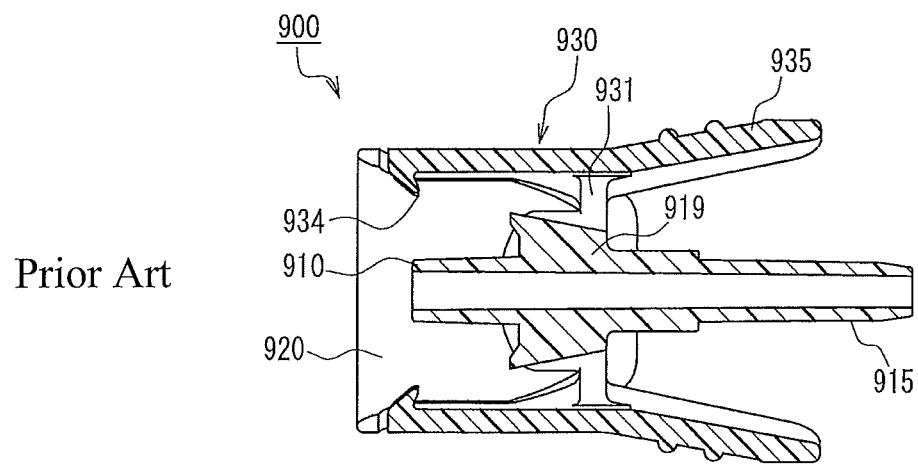
FIG. 12B is a cross-sectional view of the same.

FIG. 11 is a perspective view of the male connector 2 and the needleless port 200 in the connected and locked state. The tubes 230 connected to the outer circumferential face of the needleless port 200 are fitted into the notches 23 formed in the hood 20.

Since the notches 23 are formed in the hood 20 of the male connector 2 of Embodiment 2, the hood 20 can be connected to the coinfusion port without interfering with the tube 230.

Embodiment 2 is the same as Embodiment 1 with the exception of the above. The description of Embodiment 1 is applicable to Embodiment 2 as well. Members in the figures showing Embodiment 2 that are the same as members described in Embodiment 1 are denoted by the same reference signs, and descriptions will not be given for them.

Embodiments 1 and 2 above are merely illustrative examples. The present invention is not limited to Embodiments 1 and 2 above, and can be modified as appropriate.

The shape of the lock lever 30 can be changed as desired, as long as it includes a claw for engaging with a needleless port and has a cantilever support structure capable of elastic displacement. For example, although the lock lever 30 of Embodiments 1 and 2 above is formed by forming the approximately "U" shaped slit 21 in the hood 20, the lock lever may be provided at a location separated from the hood 20 outward of (on the side far from the male luer 10 relative to) the hood 20, for example. In this case, the fixed end of the lock lever can be provided on the outer circumferential face of the hood 20, or on the base 19 formed so as to protrude from the hood 20. The claw of the lock lever can be engaged with the needleless port via an opening formed in the hood, or at a position above the upper edge 20a of the hood.

Although the claw 34 engages with the protruding portion 112 or 212 of the needleless ports 100 and 200 in Embodiments 1 and 2, the portion of the needleless port that the claw 34 engages with may be changed appropriately according to the configuration of the needleless port. The shape and position of the claw 34 can be changed according to the portion for engaging with the needleless port.

The shape of the operation arm 35 also can be changed as desired. The amount of force F required to displace the lock lever 30 can be reduced with increasing distance in the up-down direction from the fixed end 30b to the operation portion 35a of the operation arm 35 while the operation portion 35a being below the fixed end 30b. It is preferable that the base end 35b of the operation arm 35 is provided at a position separated from the fixed end 30b such that the region of the lock lever 30 between the base end 35b and the fixed end 30b can be ensured as the elastic portion 31. Note that as the base end 35b approaches the free end 30a, the operation arm 35 needs to be made longer, and the mechanical strength of the operation arm 35 decreases. In general, it is preferable that the base end 35b of the operation arm 35 is provided at an approximately intermediate position between the fixed end 30b and the free end 30a as in Embodiments 1 and 2 above.

Although the lateral hole 12 of the male luer 10 extends along a straight line orthogonal to the central axis 10a (i.e., along the radial direction) in Embodiments 1 and 2 above, the present invention is not limited to this, and it may extend along a straight line that intersects the central axis 10a at an angle other than a right angle. The number of lateral holes 12 is also not limited to the number in the above embodiments, and can be changed as desired. Also, a configuration is possible in which the lateral hole 12 is not formed, and the channel 11 is open at the tip face 10t of the male luer 10.

Although the female connector is the needleless port including the septum 101 in Embodiments 1 and 2 above, the present invention is applicable to a male connector that can be connected in a locked state to another female connector. For example, the female connector may be a rubber plug that seals the opening of a vial container. In this case, the male member is changed to a resin needle that has a sharp tip and a liquid channel and an air channel that are independent of each other, in place of the male luer 10. Also, the claw 34 of the lock lever 30 is changed so as to engage with a constricted portion formed at the mouth of the vial container.

A cover may be attached to the male member such that the opening of the channel on tip side of the male member is not exposed when the male member is not connected to a female connector. This cover is made of a flexible material having rubber elasticity, and when the male member is connected to a female connector, the cover undergoes elastic compression deformation while the male member passes through it (see Patent Documents 3 and 4).

The male connector with a lock mechanism of the present invention can be used in any application. The present invention is applicable as a male connector that is for connection to a drug solution bag and/or a vial container and is provided in a connector for connection to a vial container, a drug solution bag, and a syringe for moving a liquid between them (e.g., see Patent Documents 3 and 4). Alternatively, the present invention is applicable as a male connector for injecting a drug solution or the like into a coinfusion port provided on a transport line for transporting a liquid such as a drug solution or blood.

INDUSTRIAL APPLICABILITY

Although there are no particular limitations on the field of use of the present invention, it can be used in a wide range as a male connector in which the state of connection to a female connector needs to be reliably maintained continuously. In particular, the present invention can be preferably used in medical fields that handle dangerous drugs (e.g., anticancer drugs), blood, and the like. Furthermore, the present invention can be used in various types of fields that handle liquids for uses other than medical use, such as food substances.

DESCRIPTION OF REFERENCE NUMERALS 1, 2 Male connector
10 Male luer (male member)
11 Channel
12 Lateral hole
20 Hood
20a Edge of hood
21 Slit
22 Bridge portion
23 Notch
30 Lock lever
30a Free end
30b Fixed end
34 Claw
35 Operation arm
35a Tip (operation portion) of operation arm
35b Base end of operation arm
100, 200 Needleless port (female connector)

The invention claimed is:

1. A male connector with a lock mechanism comprising:
a bar-shaped male member for insertion into a female connector; and
a lock mechanism for maintaining a state in which the male member is inserted into the female connector,
wherein the lock mechanism includes:
a hood that is arranged so as to surround a periphery of the male member and is for insertion of the female connector; and
a lock lever having a cantilever support structure capable of elastic displacement,
the lock lever is arranged with a free end thereof on a tip side of the male member and with a fixed end thereof on a base end side of the male member,
the lock lever includes a claw for engaging with the female connector,
an operation arm protrudes from a face of the lock lever on a side opposite to the male member, and extends toward the fixed end side,
the male connector includes the lock lever as a single lock lever,
when a pressing force in a direction approaching the male member is applied to a tip of the operation arm, the lock lever undergoes elastic deformation such that the claw moves away from the male member,
the lock lever is shaped as a thin plate with its lengthwise direction being approximately parallel to a central axis of the male member,
one end portion of the lock lever in the lengthwise direction is the free end, and the other end portion of the lock lever in the lengthwise direction is the fixed end,
a base end of the operation arm to which the lock lever is connected is provided at a position on the free end side relative to the fixed end of the lock lever, and
an elastic portion is provided between the fixed end of the lock lever and the base end of the operation arm,
wherein the operation arm extends from the base end substantially parallel to the lock lever, while the operation arm is separated from the elastic portion and the fixed end of the lock lever in a radial direction.

2. The male connector with a lock mechanism according to claim 1,
wherein the claw is provided on the free end of the lock lever.

3. The male connector with a lock mechanism according to claim 1,
wherein the operation arm is separated from the lock lever, with the exception of the base end of the operation arm.

4. The male connector with a lock mechanism according to claim 1,
wherein the operation arm extends beyond the fixed end of the lock lever in the lengthwise direction of the male member.

5. The male connector with a lock mechanism according to claim 1,
wherein an approximately "U" shaped slit is formed in the hood, and the lock lever is surrounded by the slit.

6. The male connector with a lock mechanism according to claim 5,
wherein the hood includes a bridge portion on a side on which the female connector is inserted relative to the lock lever, the bridge portion connecting portions of the hood that sandwich the lock lever in a circumferential direction.

7. The male connector with a lock mechanism according to claim 1,
wherein a pair of notches that extend along a direction parallel to the male member are formed in an edge of the hood on a side on which the female connector is inserted, and the pair of notches oppose each other across the male member.

8. The male connector with a lock mechanism according to claim 1,
wherein a channel is formed in the male member, and a lateral hole in communication with the channel is open at an outer circumferential face of the male member.

9. The male connector with a lock mechanism according to claim 1, wherein in the a thin plate of the lock lever, the free end of the lock lever, a portion of the lock lever to which the base end of the operation arm is connected, the elastic portion of the lock lever, and the fixed end of the lock lever are arranged in this order.

10. The male connector with a lock mechanism according to claim 1, wherein a central portion in a width direction of the fixed end of the lock lever is not supported directly by any radial force exerting toward an outer side of the male connector.

11. The male connector with a lock mechanism according to claim 1, wherein a free end of the operation arm is substantially coextensive with the fixed end of the lock lever.

12. The male connector with a lock mechanism according to claim 1, wherein the thin plate shape of the lock lever is not bent along the longitudinal direction of the lock lever from the fixed end of the lock lever to the claw in a condition where no pressing force is applied to the tip of the operation arm.

\* \* \* \* \*